US007785265B2

(12) United States Patent
Schätzl

(10) Patent No.: US 7,785,265 B2
(45) Date of Patent: Aug. 31, 2010

(54) MONITORING DEVICE AND METHOD

(75) Inventor: Stefan Schätzl, Weilheim (DE)

(73) Assignee: Map Medizin-Technologie GmbH, Martinsried (DE)

( * ) Notice: Subject to any disclaimer, the term of this patent is extended or adjusted under 35 U.S.C. 154(b) by 60 days.

(21) Appl. No.: 12/078,752

(22) Filed: Apr. 4, 2008

(65) Prior Publication Data

US 2008/0249427 A1    Oct. 9, 2008

(30) Foreign Application Priority Data

Apr. 5, 2007    (EP)    ................................ 07105728

(51) Int. Cl.
*A61B 5/08*    (2006.01)
(52) U.S. Cl. ...................................... 600/538; 600/529
(58) Field of Classification Search ................. 600/300, 600/529–543
See application file for complete search history.

(56) References Cited

U.S. PATENT DOCUMENTS

| | | | | |
|---|---|---|---|---|
| 4,648,407 | A * | 3/1987 | Sackner | 600/534 |
| 4,802,485 | A * | 2/1989 | Bowers et al. | 600/324 |
| 5,275,159 | A * | 1/1994 | Griebel | 600/324 |
| 5,704,345 | A * | 1/1998 | Berthon-Jones | 128/204.23 |
| 5,797,852 | A * | 8/1998 | Karakasoglu et al. | 600/529 |
| 6,142,950 | A * | 11/2000 | Allen et al. | 600/529 |
| 6,213,955 | B1 * | 4/2001 | Karakasoglu et al. | 600/529 |
| 6,368,287 | B1 * | 4/2002 | Hadas | 600/529 |
| 6,811,538 | B2 * | 11/2004 | Westbrook et al. | 600/529 |
| 6,849,049 | B2 * | 2/2005 | Starr et al. | 600/538 |
| 6,878,121 | B2 * | 4/2005 | Krausman et al. | 600/587 |
| 7,118,536 | B2 * | 10/2006 | Haberland et al. | 600/538 |
| 2002/0029004 | A1 * | 3/2002 | Starr et al. | 600/538 |
| 2002/0173707 | A1 * | 11/2002 | Lynn et al. | 600/323 |
| 2003/0055348 | A1 * | 3/2003 | Chazal et al. | 600/509 |
| 2004/0030224 | A1 * | 2/2004 | Sotos et al. | 600/300 |
| 2005/0010125 | A1 * | 1/2005 | Joy et al. | 600/529 |

(Continued)

FOREIGN PATENT DOCUMENTS

JP    10-295695    11/1998

(Continued)

OTHER PUBLICATIONS

European Search Report for EP 07105728.5 mailed Aug. 2, 2007.

(Continued)

*Primary Examiner*—Patricia C Mallari
*Assistant Examiner*—Jordan Golomb
(74) *Attorney, Agent, or Firm*—Nixon & Vanderhye P.C.

(57) ABSTRACT

The present invention relates to a method and an apparatus for providing information relating to disturbances and/or disease pattern based on a patient's breathing parameters. Preferably, the apparatus has multiple functionalities and provides information relating to different disturbances and/or disease patterns. In particular, the present invention relates to an apparatus for identifying different indications of a patient, the apparatus comprising a sensor, for sensing signals indicative of a patient's breathing, a processing unit, for processing and/or analyzing the signals, and display means for displaying the outcome of the processing and/or analysis. The corresponding method for identifying different indications of a patient comprises the steps of sensing signals indicative of a patient's breathing, processing and/or analyzing the signals, and displaying the outcome of the processing and/or analysis.

38 Claims, 5 Drawing Sheets

U.S. PATENT DOCUMENTS

| | | |
|---|---|---|
| 2005/0119586 A1* | 6/2005 | Coyle et al. ............... 600/538 |
| 2006/0155205 A1* | 7/2006 | Sotos et al. ............... 600/529 |
| 2006/0212273 A1* | 9/2006 | Krausman et al. .......... 702/189 |
| 2007/0096927 A1* | 5/2007 | Albert ..................... 340/573.1 |
| 2007/0142741 A1* | 6/2007 | Berthon-Jones et al. ..... 600/534 |
| 2007/0161913 A1* | 7/2007 | Farrell et al. ............... 600/484 |
| 2008/0009755 A1* | 1/2008 | Patangay et al. ........... 600/484 |
| 2008/0058665 A1* | 3/2008 | Scholler et al. ............ 600/529 |
| 2008/0119896 A1* | 5/2008 | Wong et al. ................. 607/2 |
| 2008/0177195 A1* | 7/2008 | Armitstead ................ 600/529 |
| 2008/0281220 A1* | 11/2008 | Sharifpour ................ 600/538 |
| 2009/0099471 A1* | 4/2009 | Broadley et al. ........... 600/532 |

FOREIGN PATENT DOCUMENTS

NZ          322972          12/1998

OTHER PUBLICATIONS

New Zealand Examination Report for co-pending Application 566715, mailed Mar. 19, 2008, 2 pages.

* cited by examiner

Periodic algorithm module

Periodic events algorithm

MONITORING DEVICE AND METHOD

CROSS REFERENCE TO RELATED APPLICATION

This application is claims the benefit of European Patent Application No. 07105728.5 filed on Apr. 5, 2007, incorporated herein by reference in its entirety.

The present invention relates to a method and an apparatus for providing information relating to disturbances and/or disease pattern based on a patient's breathing parameters. Preferably, the apparatus has multiple functionalities and provides information relating to different disturbances and/or disease patterns.

Devices and methods for providing information relating to disturbances and/or disease pattern based on a patient's breathing parameters are known in the art. However, such devices and methods are complex and complicated to use and often require the provision and use of several apparatuses or units in order to survey patient information, to analyze such information, and to provide the result of such analysis. Moreover, generally there is the need of a physician to supervise the surveying of patient information and/or to perform or control the analysis of the surveyed data with the devices or methods known in the art.

Moreover, known devices often suffer from low calculating power and inaccurate method steps or algorithms leading to the provision of imprecise or deficient information. Furthermore, the known methods and devices do not distinguish between different disturbances and/or disease patterns such as hypopnea, apnea, periodics and snoring but merely count occurring apneas.

Thus, it is an object underlying the present invention to provide a method and apparatus which overcome the deficiencies of the prior art. In particular, it is an object of the present invention to provide a method and/or device which allows an easy to use, reliable and cheap determination of a patient's, preferably different, disturbances and/or disease patterns without the need of a physician to supervise the use of the device or method.

The object underlying the present invention is achieved with the subject-matter defined in the independent claims. The dependent claims refer to preferred embodiments of the present invention.

In this application, the term patient will be used as referring to any patient or potential patient, and particularly to any person using the device and/or method according to the present invention.

The present invention provides an apparatus for identifying different indications of a patient, the apparatus comprising a sensor, for sensing signals indicative of a patient's breathing, a processing unit, for processing and/or analyzing the signals, and display means for displaying the outcome of the processing and/or analysis. The apparatus is preferably adapted as a single or closed unit device providing its functionality without the need of further devices or further processing of the derived information. Moreover, the device preferably is small in size so that it can be easily carried and used by a patient and preferably fits in a patient's pocket. The apparatus according to the present invention is adapted to perform all steps and measures necessary to provide information relating to one or more disturbances and/or disease pattern based on a patient's breathing parameters. Preferably, the apparatus provides an indication, i.e., the reason or cause for a medical action, of the patient's disturbances and/or disease pattern, preferably of breathing disturbances and/or disease characteristics.

According to a preferred embodiment the apparatus according to the present invention, also referred to as screener, is adapted to identify more than one, preferably two or more than two, and more preferably three or more than three classes or types of possible patients, disturbances and/or disease pattern. This is preferably achieved by surveying or screening signals indicative of a patient's breathing, processing and/or analyzing these signals and providing the outcome of the respective analysis as an easy distinguishable, preferably logical, e.g., YES or NO, signal. Preferably, the outcome of the respective analysis represents an indication of the risk to suffer from one or more disturbances and/or disease pattern.

Preferably, the apparatus is adapted to identify people who snore, people who suffer from sleep disordered breathing (e.g., Obstructive Sleep Apnea or OSA syndrome), and/or people who suffer from periodic disordered breathing.

People who snore, e.g., may suffer from a disturbed sleep generally at least disturb their bed partner. This need not be a medical indication for, e.g., the need for using a CPAP device or therapy, but it is at least a useful indication for the need for snoring devices. The detection of sleep disordered breathing (OSA syndrome) is considered a medical indication for, e.g., a CPAP device or therapy. The detection of periodic disordered breathing may be an indicator for a cardiological problem.

Depending on the outcome of the analysis or the indication provided by the apparatus, specific measures or therapies can or shall be considered by a patient. For example, the advice may be given to a patient to consult a physician, to get help by using a snoring device, to go to a sleep lab, and/or to see a cardiologist.

According to a preferred embodiment, the apparatus surveys or screens a signal indicative of a patient's breathing, e.g. the nasal pressure signal or the breathing flow signal, processes and/or analyses the derived signal, and provides an indication regarding the risk for one or more disturbances and/or disease pattern, preferably snoring, disordered breathing (OSA), periodic disordered breathing, and/or other disturbances and/or disease pattern detectable on a patient's breathing.

A respective apparatus is preferably adapted as a multiple use device or a single use device. If the device is a multi use device the display can preferably be reset, e.g., by an admitted person such as a physician. If the device is designed as a single use or one way device it may be thrown away or preferably recycled after use. Preferably, the apparatus does neither store nor manage raw data nor is there the requirement to upload data to a further processing device, such as a PC.

The apparatus according to the present invention is preferably comparatively small in size and, for example, has about the size of a cigarette or cigarillo package. Preferably the apparatus has a handheld and/or pocket size. More preferably, the apparatus is a closed unit and/or single unit device. Such devices, e.g., provide a functional unit without depending on the connection to additional hardware or software in order to be operative and/or to fulfill the desired purpose.

The apparatus according to the present invention is particularly advantageous in that it is adapted to provide an indication for a number of different medical indications, at low costs, requiring no calibration, and/or allowing easy handling wherein no further analysis of the received data by a personal computer or the like is required. A further advantage of the present apparatus is that the above features and advantages of the present apparatus are achieved in a single or closed, preferably hand-held, unit. This functional unit preferably has a handheld and/or pocket size and provides easy determinable and reliable information as an output and is easy to handle by a patient, i.e., a medically untrained person.

In the following, the apparatus and method according to the present invention will be further described by way of example and by reference to the figures of which FIG. 1 shows an exemplary embodiment of a device according to the present invention which is suitable for providing information regarding three different disturbances;

Figure 1:
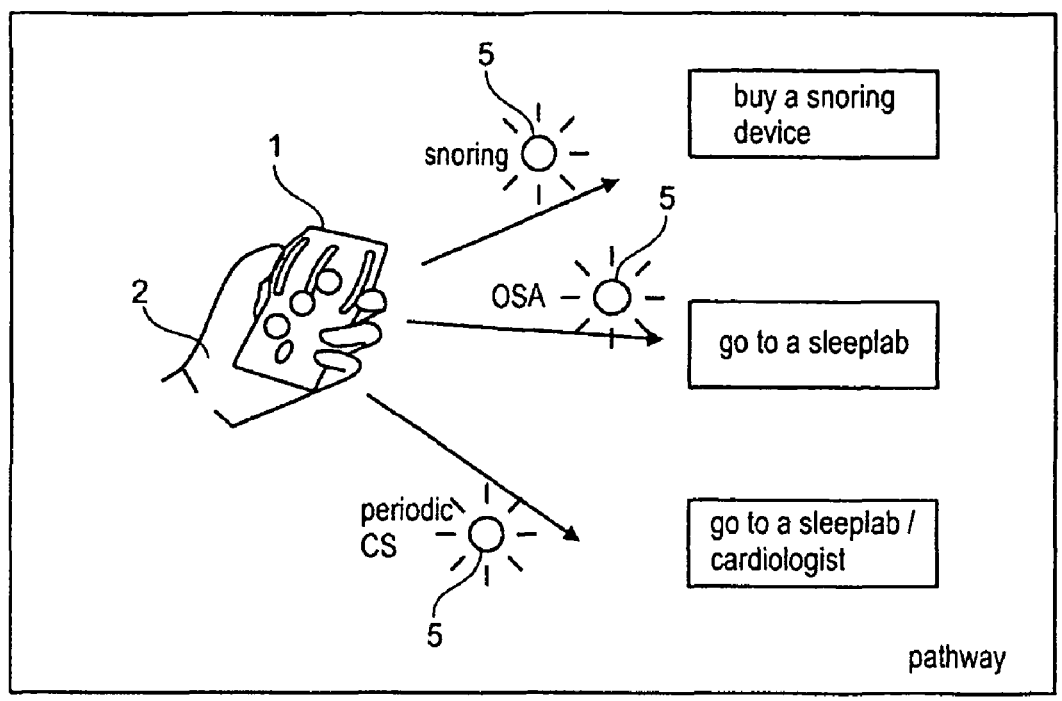
Figure 2:
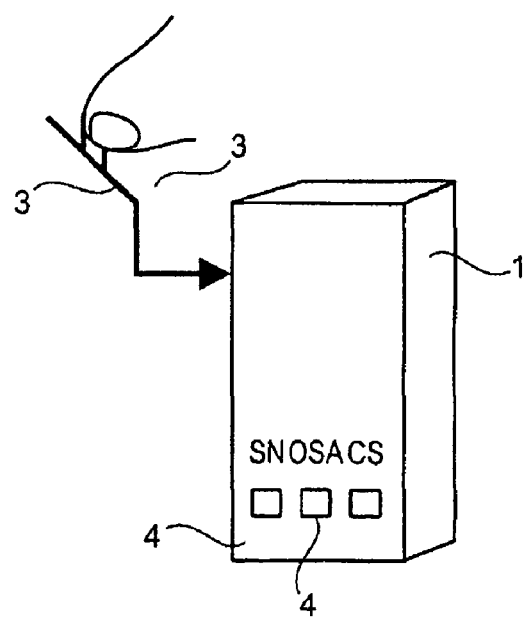
FIG. 2 shows a schematic structure and concept of a preferred device and method according to the present invention.

FIGS. 1 and 2 show an apparatus 1 for identifying different indications of a patient according to a preferred embodiment of the present invention. The apparatus is of a hand-held or pocket size so that it can easily be carried and used by a patient. A preferred size of the apparatus is apparent from the also depicted general size of a human hand 2. The apparatus 1 comprises a sensor (not shown) for sensing signals indicative of a patient's breathing. Such sensor is preferably a pressure sensor, a differential pressure sensor, and or a flow sensor for sensing flow parameters of a patient's breathing. Preferably, a patient's breathing is guided by a suitable and generally known structure from a patient's mouth or preferably nose via a hose structure to the apparatus and the sensor, respectively. Preferably, the apparatus comprises a nasal cannula 3, as e.g. shown in FIG. 2. The apparatus further comprises a processing unit, for processing and/or analyzing the breathing signals derived from the patient's breathing and provided by the sensor. The result or outcome of this processing and/or analysis is displayed by an indicator or display means 4. The result of the analysis is preferably displayed as an easy distinguishable signal, preferably a logical YES or NO signal. As shown in FIG. 1, the result is preferably indicated by the activation of a light emitting device 5, such as an LED, which is either on or off. The visualization of the result may also be performed by using different colors of the display, e.g., green for a positive result and red for a negative result. Preferably, the apparatus analyses the nasal pressure signal and gives an indication of the risk for certain disturbances such as OSA and related problems.

The device according to FIG. 1 or 2 allows the detection of three different disturbances and/or disease patterns. Preferably, the screener is adapted to identify three classes of patients, namely people who snore, people who suffer from sleep disordered breathing (obstructive sleep apnea or OSA-syndrome), and people who suffer from periodic disordered breathing (Cheyne Stokes breathing or periodic CS). The latter may be an indicator for a cardiological problem.

According to preferred embodiments, other or further disturbances may be detected by the device according to the present invention.

As shown, the apparatus 1 is preferably a closed or single unit. The apparatus is furthermore preferably of a small size and can be easily used by a patient at home or in a private environment. Preferably, the apparatus comprises different means which are adapted to perform certain measures, as discussed in this application, so that no further means or method steps are required to perform the discussed analysis of a patient's breathing and to provide the result as an easy distinguishable information. The apparatus preferably comprises an energy source such as an accumulator or a rechargeable battery.

Figure 3:
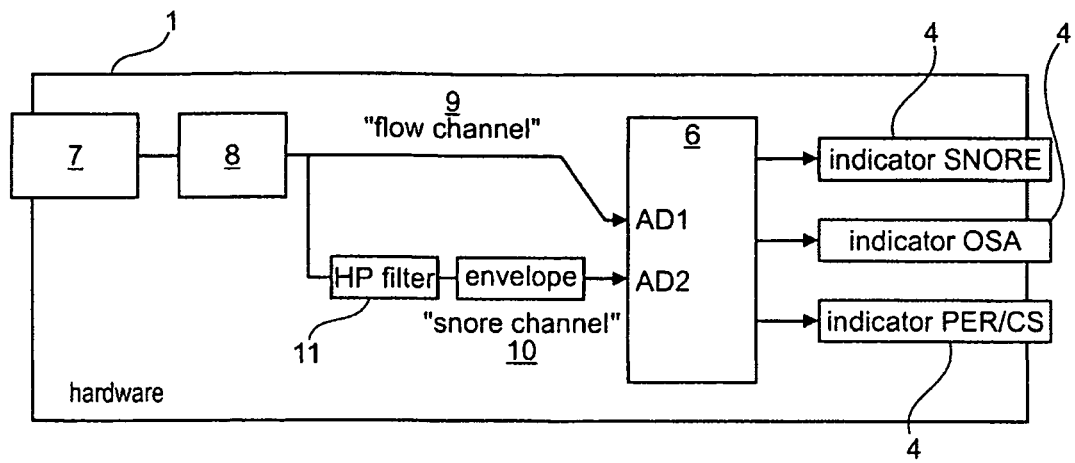
FIG. 3 shows a preferred schematic structure and concept of a device and method according to the present invention.

According to a preferred embodiment, as shown, e.g., in FIG. 3, the apparatus comprises means for performing algorithms or the like in order to process and analyze the input signal sensed by the sensing unit. Preferably, the apparatus comprises a controller 6, preferably a PIC controller, and a pressure sensor 7, preferably a low cost pressure sensor.

Preferably, particularly to avoid sensor calibration at production time the sensor 7 is AC coupled to an A/D converter. Preferably, the sensor is connected to the processor 6 via an AC coupling 8. Preferably, the sensor 7 provides information to the controller 6 via a first channel 9 and a second channel 10.

The nasal pressure signal, as sensed by the pressure sensor 7, is preferably provided to the controller 6 via a first channel 9, e.g., a flow channel. Preferably, the nasal pressure signal is connected to an A/D1 input of the controller 6.

Preferably, there is provided a second channel 10, such a snore channel, for providing information regarding the sensed pressure signal to the controller 6. Preferably, particularly to avoid high sampling rates but still allow the reliable detection of snoring, an envelope of the original pressure signal is formed by an analog circuit. The envelop signal is preferably connected to an A/D2 input of the controller 6.

In other words, according to a preferred embodiment, the sensed pressure signal is firstly directly provided to the controller 6 via a first channel 9, also referred to as flow channel. Secondly, the sensed pressure signal is additionally processed, i.a., by means of, e.g., a filter 11 such as an HP Filter and/or an envelope means 12 for creating an envelope signal or an envelope curve, and provided to the controller 6 via a second channel 10, also referred to a snore channel, as an envelope signal.

Preferably the controller 6 implements or is adapted to perform algorithms for different, according to an preferred embodiment three, indicators. The result of the indication performed is preferably visualized by means of at least one, preferably three and more, preferably a number corresponding to the number of possible indication, indicators or display elements 4. The display means 4 are preferably simple LEDs 5 or non-volatile display elements 13, such as in single-use-devices, to document the result of the study. As shown in FIG. 3, the controller 6 provides information to three different indicators 4, namely a SNORE indicator, an OSA indicator, and a periodic/CS indicator.

According to a preferred embodiment, the result of the indication performed by the apparatus 1 is displayed by a reusable display, such as for multiuse devices. Such multiuse display is, e.g., an LED 5 or the like. Preferably, also in multiuse devices the result of indication is shown by a permanent signal which the patient using the device has to show to a chemist or doctor. Preferably, the display of the indication or result has to be cleared afterwards by an authorized user.

For single use devices, the result or indication can be shown by a non-volatile or permanent indicator 13. Such indication or display can then be shown to the doctor before the device is thrown away, comparable to the result of well known pregnancy tests. Preferably, the indicator is realized by a small window 14 in the housing 15 of the apparatus 1 comprising an inlet of, e.g., thermal paper or a thermal sensitive lacquer 16. Such paper or lacquer is, according to a preferred embodiment, blackened by a heat source or the like 17, such as an SMD resistor. Thereby, a permanent mark can be achieved at the respective display fields indicating diagnoses for disturbances as referred to above, e.g., such as "snoring", "OSA", or "periodic/CS".

Figure 4:
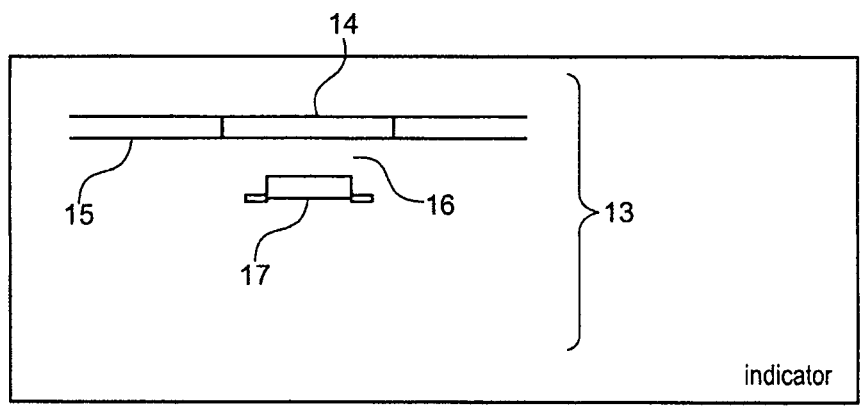
FIG. 4 shows preferred schematic concept or structure of a non-volatile display or indicator according to the present invention.

FIG. 4 shows a part of the housing 15 of the apparatus 1 according of a preferred embodiment of the present invention having a transparent window 14 under which there is placed a thermal indicator 16, e.g., a piece of thermal paper. Underneath or in the vicinity of this thermal indicator there is arranged a heat source 17, such as an SMD resistor. The activation of the SMD resistor by the controller 6 will result in the production of heat which will result in a change of color of the thermal indicator thereby providing a certain indication.

Preferably, the controller 6 comprises a data acquisition module 18 that is adapted to read out the input to the controller 6, preferably the input channels A/D1 and A/D2 from the analog inputs. According to the preferred embodiment as discussed above, when an envelope signal is provided via the snore channel 10 by means of a filter 11 and or an envelope means 12, a sampling rate of about 5 Hz to 20 Hz and preferably about 10 Hz is preferably sufficient.

The flow signal as referred to herewith is preferably a pressure or a flow signal and preferably a nasal pressure or flow signal. Such signal is further referred to as flow or flow signal but is also meant to cover pressure or pressure signals.

Preferably, the flow and snoring signal as provided to the controller 6 via the flow channel 9 and the snore channel 10, respectively, will be provided to different processing modules of the processor to, e.g., perform a different processing of or different algorithms on these signals. Preferably, the apparatus according to the present invention comprises at least one and more preferably at least three modules that are adapted to perform at least one different analysis of the flow channel signal and/or snoring channel signal. The algorithms preferably used with the apparatus according to the present invention are preferably simple enough to fit into a low cost processor but still reliable and good enough to have sufficient sensitivity and specificity required for a screening device. These modules or algorithm modules preferably calculate separate risk indicators. The raw data retrieved by the data acquisition module 18 and underlying the calculation of risk indicators performed by the apparatus 1 preferably do not need to be stored. Preferably, the apparatus comprises two FIFOs for characteristics (basic and combined) to handle the data exchange between the different modules.

Figure 5:
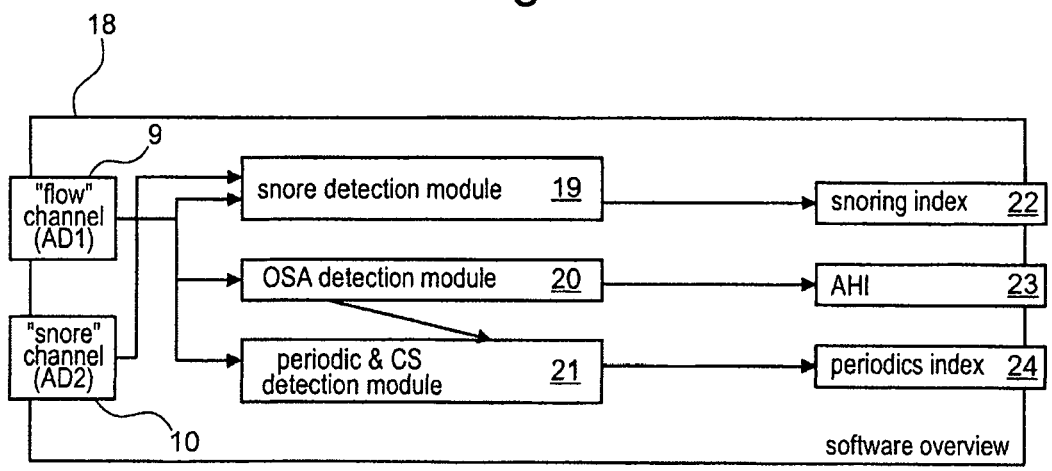
FIG. 5 shows a preferred schematic structure and concept of a device and method according to the present invention.

FIG. 5 shows a preferred data acquisition module 18 having inputs A/D1 for the signal of flow channel 9 and A/D2 for the signal of the snore channel 10. The data acquisition module 18 further comprises one or more modules, preferably depending on the disturbances and/or disease pattern to be indicated. Preferably, the data acquisition module 18 comprises the a snore detection module 19, an OSA detection module 20 and a periodic/CS detection module 21, as shown in FIG. 5.

The snore detection module 19 preferably processes the signals provided via the flow channel 9 and the signal provided via the snore channel 10 in order to generate a snoring index 22. The OSA detection module 20 preferably processes the signals provided via the flow channel 9 in order to generate a risk indicator based on apnea and hypopnea, for example a AHI 23. The periodic & CS detection 21 module preferably processes the signals provided via the flow channel 9 in order to generate a periodic index 24. Based on the snoring index 22, the AHI 23, and the periodic index 24 the processor 6 will control the indicator or display 4.

Figure 6:
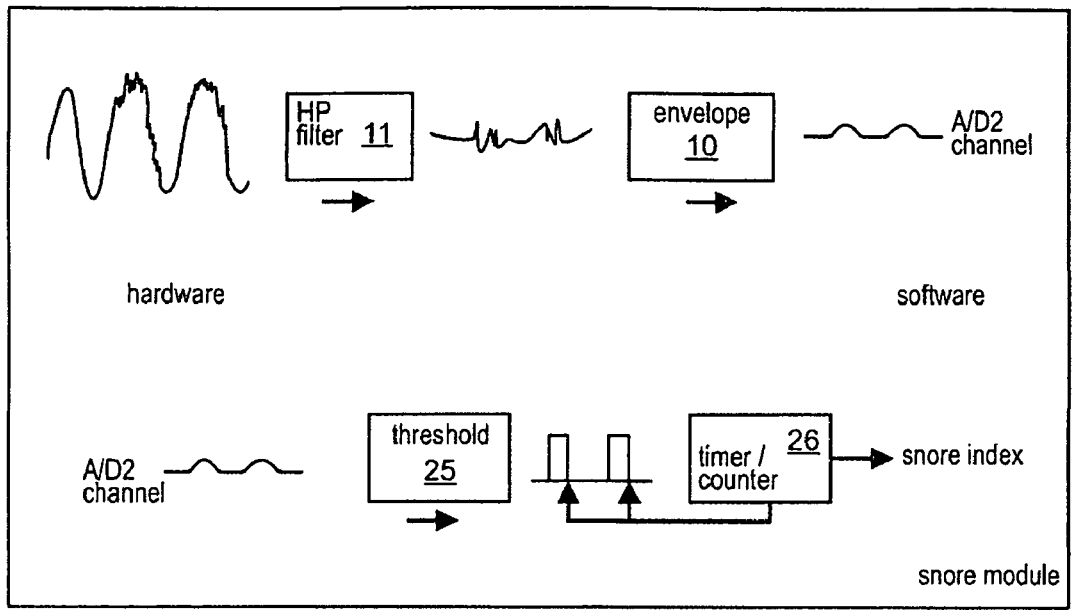
FIG. 6 shows the schematic structure of a preferred processing and analyzing algorithm according to the present invention.

The snore module 19, as shown in FIG. 6, preferably uses the input signal of cannel 10 providing the signal of the sensor 7 and the A/D converter 8. On this snore channel 10 the signal as output by the sensor 7 and the converter 8 is preferably processed by a filter means 11 and an envelope means 12 creating an envelope signal. Filter means 11 is preferably a high pass filter having a cut-off frequency of about 10 Hz. The upper cut-off frequency is preferably at approximately 50 to 100 Hz.

Via channel 10 there is thus preferably provided the envelope of the flow signal. Furthermore, the controller 6 and the snore module 19, respectively, preferably comprises a threshold detector means which is adapted to analyze the envelope signal provided via channel 10 and to detect the length of signal snoring events comprised in that signal. Preferably there is a minimum time length criterion for snoring events in order to prevent the snore module from detecting artefacts.

The snore module 19 furthermore preferably comprises a timer or counter 26 for comparing the number of snoring events to a preset internal time base or threshold and that calculates a snoring index 22.

Figure 7:
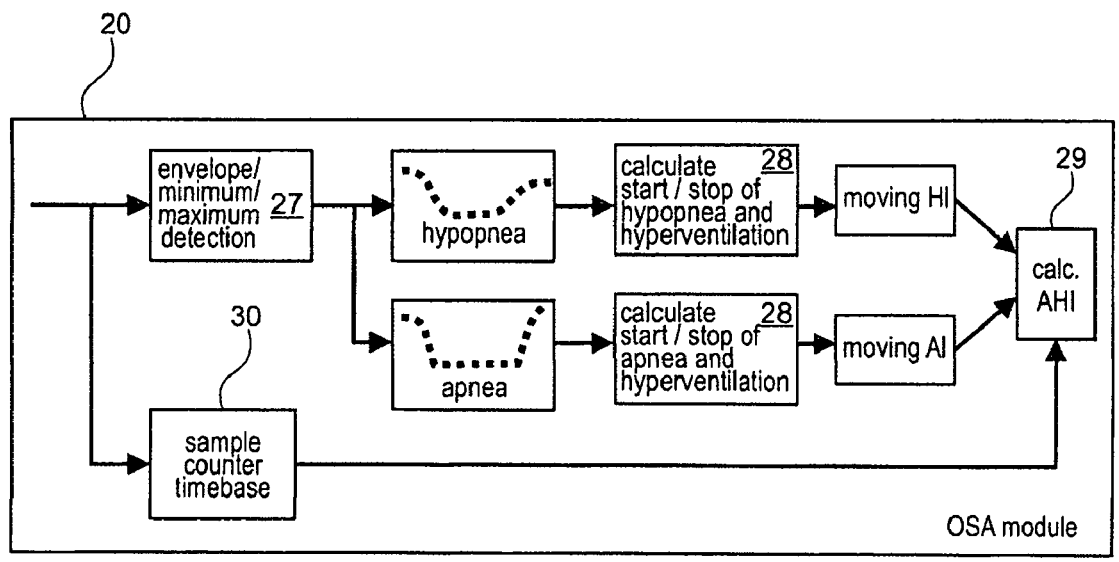
FIG. 7 shows a preferred schematic flow diagram of a preferred schematic structure and concept according to the present invention.

Preferably, the apparatus 1 comprises an OSA module 20. The schematic structure of a preferred OSA detection module 20 is shown in FIG. 7. Preferably, the module 20 is adapted to use envelope and threshold (time and amplitude) algorithms to detect a reduction of the flow envelope. This is similar to a standard thermistor analysis. The differentiation between apnea and hypopnea can, according to the preferred embodiment, be discarded if just an AHI or respiratory disturbance index is calculated to trigger the OSA indicator. However, the differentiation between apnea and hypopnea with separate thresholds is preferably used, particularly to increase spectivity within such algorithm.

The OSA detection module 20, as shown in FIG. 7, preferably receives the signal provided via flow channel 9 as an input. The OSA detection module preferably comprises a detection means 27 for detection the envelope, the maximum and/or the minimum of the input signal. Based on the output of the detection means 27 at least one calculation means 28 calculates the start and/or stop of an apnea, hypopnea and/or hyperventilation. Preferably, there are provided two calculation means 28, one for calculating the start/stop of hypopnea and hyperventilation and one for calculating the start/stop of apnea and hyperventilation. The calculation means 28 provides a moving hypopnea index HI and/or a moving apnea index AI as an output. Based on the moving hypopnea index HI, the moving apnea index AI and information provided by a counter means 30 a AHI calculation means 29 calculates an apnea/hypopnea index 23. The counter means 30 calculates sample counters as a timebase on the basis of the signal provided via flow channel 9.

Preferably, the OSA module provides additional information such as the length of apneas, hypopneas and/or hyperventilations. According to a preferred embodiment, such information is used in the periodic/CS module 21 as further described below.

Figure 8:
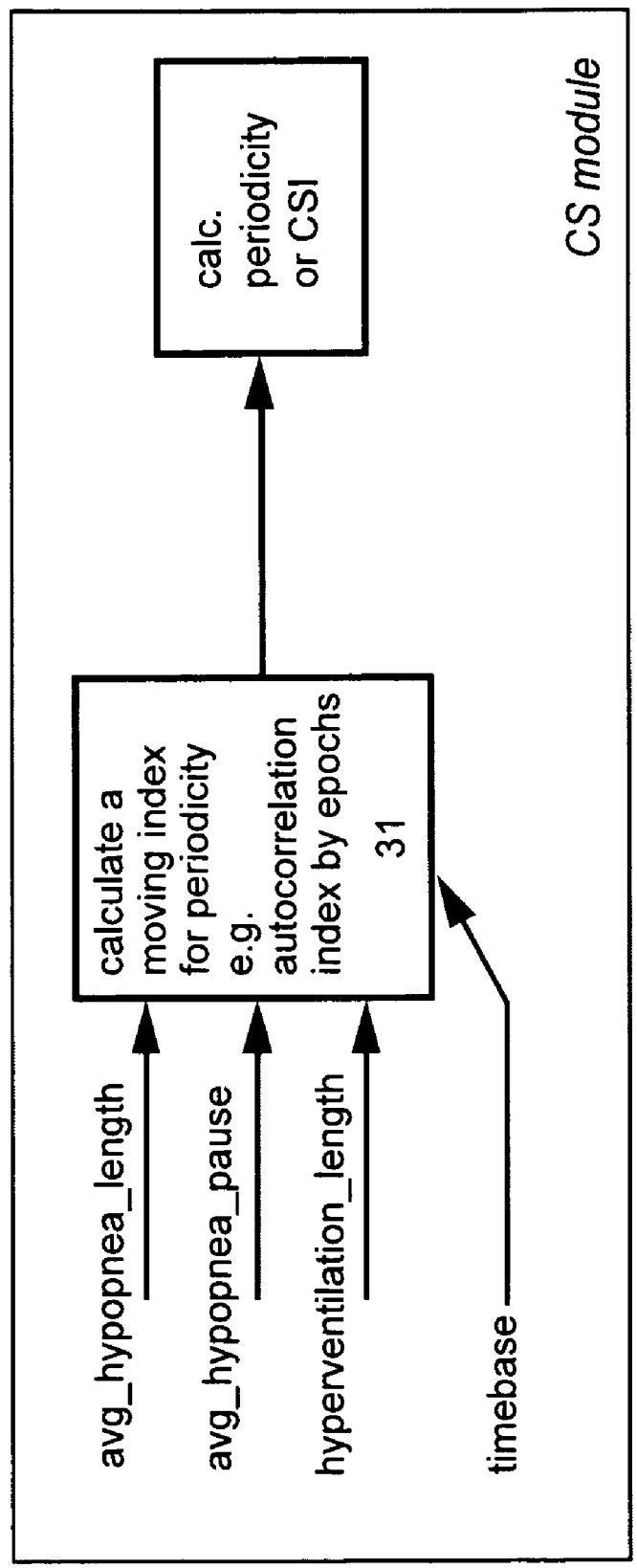
FIG. 8 shows a schematic basic structure and concept according to a preferred embodiment of the present invention.

The periodic and CS detection module 21, e.g. as shown in FIG. 8, for detecting periodic and Cheyne Stokes patterns preferably performs its processing on the basis of hypopnea pause and length information (which includes apnea as a special case). Preferably, the periodic and CS calculation means 21 comprises an envelope/minimum/calculation means (not shown) as referred to with regard to FIG. 7 and/or and index calculation means 31 for calculating a moving index for periodicity, e.g., for autocorrelation index by epochs. Preferably, the index calculation means receives information regarding the average hypopnea length, the average hypopnea pause and/or the hyperventilation length as input parameters as well as the timebase information as referred to above with regard to counter means 30. The respective information relating to hypopnea automatically include apnea information as a special case. Preferably, the periodic and CS detection module 21 and the index calculation means 31 provides the periodic index 24 comprising an periodicity index and/or a Cheyne Stokes index as an output.

Such periodic or CS module 21 preferably detects central periodic breathing patterns from the nasal cannula signal as provided, e.g., via flow channel 9. Preferably, the module for detection of CS 21 uses the fact that the shape of the envelop of flow maxima is periodic. Preferably, the periodic or CS module 21 abstracts the flow curve in falling gradients (FG) and rising gradients (RG) as well as apneas or hypopneas with a horizontal shape. An indicator for periodic apneas can be calculated from the frequency of occurrences of the RG-FG complex and short epochs. If higher spectivity is needed, the maxima of the RG-FG complexes can be auto-correlated to get a number for the regularity.

Figure 9:
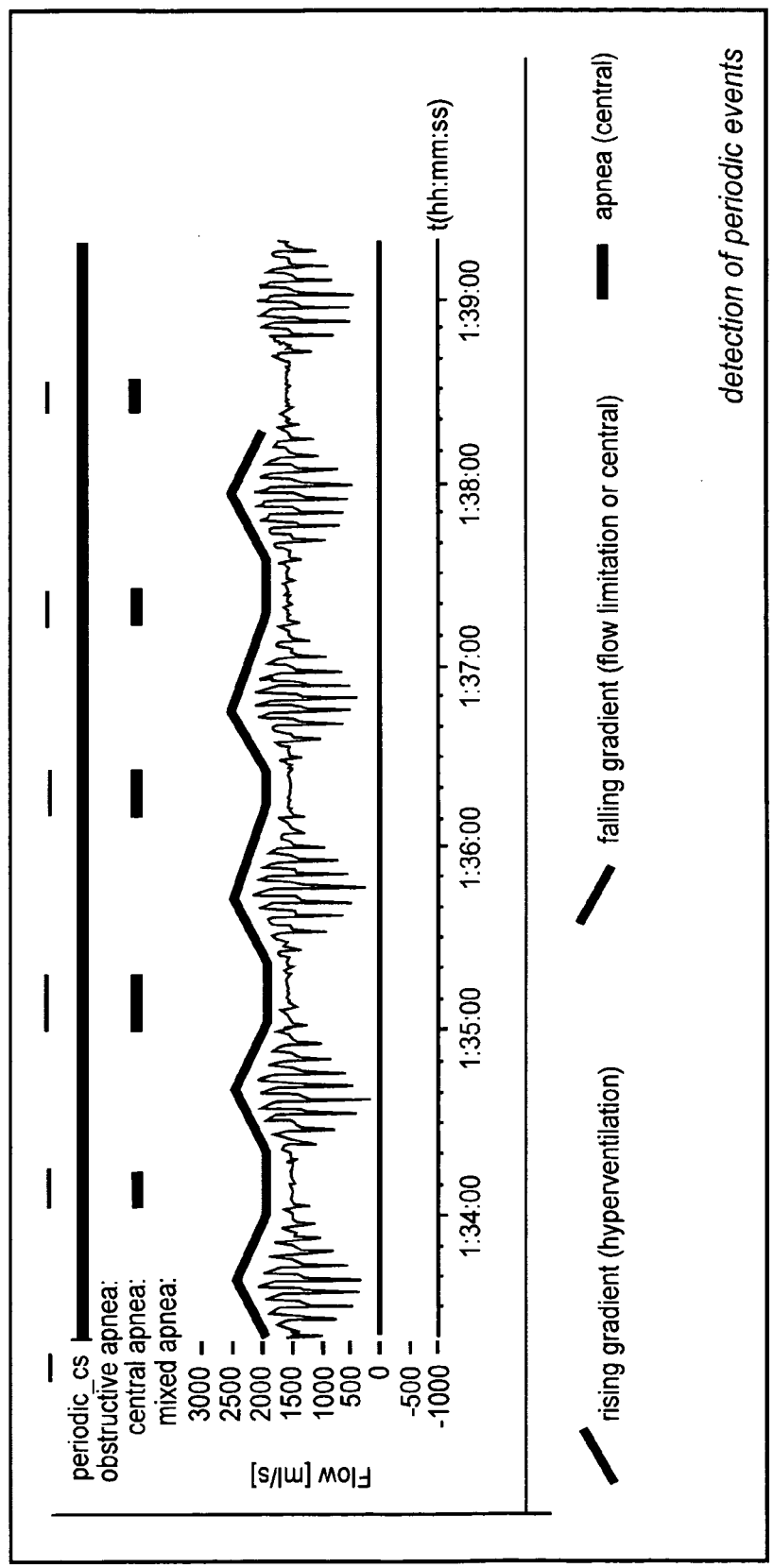
FIG. 9 shows the detection of periodic events according to a preferred embodiment of the present invention.

The detection of periodic events is shown in e.g. FIG. 9 identifying rising gradients RG, which are particularly informative with regard to hyperventilation, falling gradients FG, with are particularly informative with regard to flow limitation of central breathing disorders, and apneas (central) with a horizontal shape on the basis of an exemplary flow curve (flow over time).

It is expected that a normal or just "OSA" disordered breathing pattern will not have an adequate number of RG-FG complexes to indicate "periodic". Thus, periodicity is not determined via FFT or the like.

Preferably, the apparatus comprises a pressure and/or flow sensor, analog electronics, a PIC controller and a three color LED The apparatus according to the present invention is preferably adapted as a single unit or closed unit device for single or multi uses. The apparatus is easy to use and provides a reliable and easy to determine information as a output. This allows the apparatus to be used at home by a patient. Once a patient has used the device, the results or indications of such use can be shown to a doctor or physician. There is no need to provide specific means or adaptors to read out the indication achieved by the apparatus according to the present invention. Rather, the information can be read out easily and reliably even by an unskilled person.

The apparatus according to the present invention is particularly advantageous in that it provides indicators for different medical indications, has low material costs, requires no calibration, is easy to handle, and/or does not require further processing of the sensed date by a PC or the like.

The invention claimed is:

1. An apparatus for identifying different indications of a patient, the apparatus comprising
    a sensor configured to sense signals indicative of a patient's breathing;
    a processing unit configured to process and/or analyze the signals by generating flow and snore channel signals;
    a snore detection module configured to calculate a snoring index based on the flow and snore channel signals;
    an Obstructive Sleep Apnea (OSA) detection module configured to calculate an apnea/hypopnea index based on the flow channel signal;
    a periodic breathing and/or Cheyne-Stokes (CS) detection module configured to calculate a periodic breathing index and/or CS index based on the flow channel signal and output from the OSA detection module; and
    a display configured to display data related to output from the snore, OSA, and periodic breathing and/or CS detection modules.

2. The apparatus according to claim 1, wherein the display is further configured to display data related to output from the snore, OSA, and periodic breathing and/or CS detection modules as logical YES or NO indicators, the logical YES or NO indicators corresponding the presence or absence of patient snore, OSA, and periodic breathing and/or CS, respectively.

3. The apparatus according to claim 2, wherein the indicators comprise LEDs.

4. The apparatus according to claim 1, wherein the apparatus is a closed unit.

5. The apparatus according to claim 1, wherein the apparatus is a handheld and/or pocket size device.

6. The apparatus according to claim 1, wherein the apparatus comprises an energy source.

7. The apparatus according to claim 6, wherein the energy source is an accumulator or a rechargeable battery.

8. The apparatus according to claim 1, wherein the apparatus further comprises at least one A/D converter.

9. The apparatus according to claim 1, wherein the snore detection module includes a filter and an envelope generator.

10. The apparatus according to claim 9, wherein the filter has a lower frequency cutoff of about 10 Hz.

11. The apparatus according to claim 10, wherein the filter has an upper frequency cutoff of about 50-100 Hz.

12. The apparatus according to claim 1, wherein the apparatus is a single-use apparatus.

13. The apparatus according to claim 1, further comprising first and second A/D converters, the first A/D converter being usable in the generation of the flow channel signal and the second A/D converter being usable in the generation of the snore channel signal.

14. A portable handheld diagnostic apparatus, comprising:
    a sensor configured to sense signals indicative of a patient's breathing;
    a processing unit configured to generate flow and snore channel signals based on the signals sensed by the sensor;
    a snore detection module configured to calculate a snoring index based on the flow and snore channel signals;
    an Obstructive Sleep Apnea (OSA) detection module configured to calculate an apnea/hypopnea index based on the flow channel signal;
    a periodic breathing and/or Cheyne-Stokes (CS) detection module configured to calculate a periodic breathing index and/or CS index based on the flow channel signal and output from the OSA detection module; and
    a display comprising a plurality of logical YES/NO indicators, the YES/NO indicators being actuatable in dependence on calculations from the snore, OSA, and periodic breathing and/or CS detection modules.

15. The apparatus according to claim 14, further comprising first and second A/D converters, the first A/D converter being usable in the generation of the flow channel signal and the second A/D converter being usable in the generation of the snore channel signal.

16. The apparatus according to claim 14, wherein the snore detection module includes a filter and an envelope generator, the filter having a lower frequency cutoff about 10 Hz and an upper frequency cutoff of about 50-100 Hz.

17. The apparatus according to claim 14, wherein the periodic breathing and/or CS detection module is configured to calculate a periodic breathing index based on rising and falling gradients.

18. The apparatus according to claim 14, further comprising a nasal cannula.

19. The apparatus according to claim 14, wherein the periodic breathing and/or CS detection module is configured to calculate both a periodic breathing index and/or a CS index in dependence on the patient's breathing.

20. A method for identifying different indications of a patient via an apparatus usable by the patient, the method comprising
sensing signals indicative of a patient's breathing using a sensor connected to the apparatus;
processing and/or analyzing the signals by generating flow and snore channel signals using a processor of the apparatus;
calculating a snoring index based on the flow and snore channel signals via a snore detection module;
calculating an apnea/hypopnea index based on the flow channel signal via an Obstructive Sleep Apnea (OSA) detection module;
calculating a periodic breathing index and/or Cheyne-Stokes (CS) index based on the flow channel signal and output from the OSA detection module via a periodic breathing and/or CS detection module; and
displaying data related to output from the snore, OSA, and periodic breathing and/or CS detection modules.

21. The method according to claim 20, further comprising displaying data related to output from the snore, OSA, and periodic breathing and/or CS detection modules as logical YES or NO indicators, the logical YES or NO indicators corresponding the presence or absence of patient snore, OSA, and periodic breathing and/or CS, respectively.

22. The method according to claim 21, wherein the indicators comprise LEDs.

23. The method according to claim 20, wherein the apparatus is a closed unit.

24. The method according to claim 20, wherein the apparatus is a handheld and/or pocket size device.

25. The method according to claim 20, wherein the apparatus comprises an energy source.

26. The method according to claim 25, wherein the energy source is an accumulator or a rechargeable battery.

27. The method according to claim 20, wherein the apparatus further comprises at least one A/D converter.

28. The method according to claim 20, wherein the snore detection module includes a filter and an envelope generator.

29. The method according to claim 28, wherein the filter has a lower frequency cutoff of about 10 Hz.

30. The method according to claim 29, wherein the filter has an upper frequency cutoff of about 50-100 Hz.

31. The method according to claim 20, wherein the apparatus is a single-use apparatus.

32. The method according to claim 20, further comprising:
generating the flow channel signal via a first A/D converter of the apparatus; and
generating the snore channel signal via a second A/D converter of the apparatus.

33. A method of diagnosing a patient using a portable handheld diagnostic apparatus, the method comprising:
sensing, via a sensor of the apparatus, signals indicative of the patient's breathing;
generating, via a processor, flow and snore channel signals based on the signals sensed by the sensor;
calculating, via a snore detection module, a snoring index based on the flow and snore channel signals;
calculating, via an Obstructive Sleep Apnea (OSA) detection module, an apnea/hypopnea index based on the flow channel signal;
calculating, via a periodic breathing and/or Cheyne-Stokes (CS) detection module, a periodic breathing index and/or CS index based on the flow channel signal and output from the OSA detection module; and
selectively actuating a plurality of logical YES/NO indicators provided to the apparatus, in dependence on calculations from the snore, OSA, and periodic breathing and/or CS detection modules.

34. The method according to claim 33,
generating the flow channel signal via a first A/D converter of the apparatus; and
generating the snore channel signal via a second A/D converter of the apparatus.

35. The method according to claim 33, wherein the snore detection module includes a filter and an envelope generator, the filter having a lower frequency cutoff about 10 Hz and an upper frequency cutoff of about 50-100 Hz.

36. The method according to claim 33, further comprising calculating, via the periodic breathing and/or CS detection module, the periodic breathing index based on rising and falling gradients.

37. The method according to claim 33, wherein the apparatus further comprises a nasal cannula.

38. The method according to claim 33, further comprising calculating, via the periodic breathing and/or CS detection module, both the periodic breathing index and/or the CS index in dependence on the patient's breathing.

* * * * *